(12) United States Patent
Boguraev et al.

(10) Patent No.: US 8,510,327 B2
(45) Date of Patent: Aug. 13, 2013

(54) METHOD AND PROCESS FOR SEMANTIC OR FACETED SEARCH OVER UNSTRUCTURED AND ANNOTATED DATA

(75) Inventors: Branimir Konstantinov Boguraev, Bedford, NY (US); Eric William Brown, New Fairfield, CT (US); Youssef Drissi, Peekskill, NY (US); David Angelo Ferrucci, Yorktown Heights, NY (US); Paul Turquand Keyser, New York, NY (US); Anthony Tom Levas, Yorktown Heights, NY (US); Dafna Sheinwald, Nofit (IL)

(73) Assignee: International Business Machinees Corporation, Armonk, NY (US)

( * ) Notice: Subject to any disclaimer, the term of this patent is extended or adjusted under 35 U.S.C. 154(b) by 63 days.

(21) Appl. No.: 13/104,111

(22) Filed: May 10, 2011

(65) Prior Publication Data

US 2012/0078955 A1    Mar. 29, 2012

Related U.S. Application Data

(60) Provisional application No. 61/386,051, filed on Sep. 24, 2010.

(51) Int. Cl.
*G06F 7/06*      (2006.01)
*G06F 17/30*     (2006.01)

(52) U.S. Cl.
USPC ............................ 707/769; 707/803; 707/713

(58) Field of Classification Search
USPC ................... 707/999.004, 999.102, 713, 739, 707/769, 803
See application file for complete search history.

(56) References Cited

U.S. PATENT DOCUMENTS

| 5,421,008 | A | 5/1995 | Banning |
| 6,208,985 | B1 | 3/2001 | Krehel |
| 6,426,761 | B1 * | 7/2002 | Kanevsky et al. ............ 715/788 |
| 6,725,227 | B1 | 4/2004 | Li |
| 6,938,036 | B2 | 8/2005 | Dettinger |
| 6,947,928 | B2 | 9/2005 | Dettinger |
| 7,149,731 | B2 | 12/2006 | Dettinger |
| 7,188,105 | B2 | 3/2007 | Dettinger |

(Continued)

FOREIGN PATENT DOCUMENTS

DE    102004036500    7/2004

OTHER PUBLICATIONS

Xian Ding et al, An ontology-based semantic expansion search model using semantic condition transform, 2009.

(Continued)

*Primary Examiner* — Bruce Moser
(74) *Attorney, Agent, or Firm* — August Law, LLC; George Willinghan (57) ABSTRACT

A semantic query over a corpus of data is constructed using a graphical user interface to create an aggregation of graphical representations of annotations associated with a plurality of data elements contained within the corpus of data and graphical representations of search terms contained within the plurality of data elements. The aggregation includes at least one annotation and at least one search term. The relative positions of the graphical representations of the annotations and the search terms are manipulated within the aggregation within the graphical user interface to express relationships among the annotations and search terms, yielding a visual spatial representation of the semantic query. The annotations, search terms and expressed relationships define the semantic query that is used to search the corpus of data.

22 Claims, 6 Drawing Sheets

(56) References Cited

U.S. PATENT DOCUMENTS

| | | | |
|---|---|---|---|
| 7,333,981 B2 | 2/2008 | Dettinger | |
| 7,526,425 B2 | 4/2009 | Marchisio | |
| 7,529,732 B2 | 5/2009 | Liu | |
| 7,548,933 B2 | 6/2009 | Krishnamurthy | |
| 7,558,778 B2 * | 7/2009 | Carus et al. | 1/1 |
| 7,593,929 B2 | 9/2009 | Dettinger | |
| 7,617,196 B2 | 11/2009 | Dettinger | |
| 7,702,645 B2 | 4/2010 | Khushraj | |
| 2005/0216457 A1 * | 9/2005 | Walther et al. | 707/4 |
| 2010/0235353 A1 * | 9/2010 | Warnock et al. | 707/723 |

OTHER PUBLICATIONS

Moller, M. et al, RadSem: semantic annotation and retrieval for medical images,2009.

Cao, TH. et al.; A robust ontology-based method for translating natural language queries to conceptual graphs, 2008.

Urbain, J. et al.; Probabilistic passages models for semantic search search of genomics literature, 2008.

Kudelka, M. et al.; Semantic Analysis of Web Pages Using Web Patterns, 2006 (IEEE).

D. Braga, A. Campi, and S. Ceri, XQBE (XQuery by Example): A Visual Interface to the Standard XML Query Language, ACM Transactions on Database Systems 30.2 (2005) 398-443.

Irna M.R. Evangelista Filha, Altigran S. Da Silva, Alberto H.F. Laender, and David W. Embley, "Using Nested Tables for Representing and Querying Semistructured Web Data," in Anne Banks Pidduck, John Mylopoulos, Carson C. Woo, and M. Tamer Ozsu, edd., Advanced Information Systems Engineering LNCS 2348 (2002) 719-723.

Petropoulos et al, (Querying and Reporting Semistructured Data, QURSED, 2002.

Li et al, "XGI: A Graphical Interface for XQuery Creation," in AMIA Annu Symp Proc . (2007) 453-457.

Bouzegboub et al, Search and Composition of Learning Objects in a Visual Environment, in Learning in the Synergy of Multiple Disciplines Lecture Notes in Computer Science, Springer: Berlin & Heidelberg, vol. 5794 (2009) ISSN 0302-9743 (Print) 1611-3349 (Online), ISBN 978-3-642-04635-3.

S. Jeromy Carriere and Rick Kazman, "WebQuery: searching and visualizing the Web through connectivity," Computer Networks and ISDN Systems 29.8-13 (Sep. 1997) 1257-1267 = Papers from the Sixth International World Wide Web Conference.

Wen-Syan Li and Junho Shim, "Facilitating complex Web queries through visual user interfaces and query relaxation," in Computer Networks and ISDN Systems ,vol. 30, Issues 1-7, Apr. 1998, pp. 149-159 = Proceedings of the Seventh International World Wide Web Conference.

Wen-Syan Li, Junho Shim and K. Selcuk Candan, "WebDB: A System for Querying Semi-structured Data on the Web," Journal o/Visual Languages & Computing 13.1 (Feb. 2002) 3-33.

Chabane Djeraba, Marinette Bouet, and Henri Briand, "Concept-Based Query in Visual Information Systems," IEEE International Forum on Research and Technology Advances in Digital Libraries ADL'98 ,pp. 299-308.

Sriram Raghavana and Hector Garcia-Molina, "Complex Queries over Web Repositories," Proceedings 2003 VLDB Conference (2003) 33-44.

Gustavo O. Arocena, Alberto O. Mendelzon, and George A. Mihailal, "Applications of a Web query language," Computer Networks and ISDN Systems ,29.8-13 (Sep. 1997) 1305-1316 = Papers from the Sixth International World Wide Web Conference.

G. Barzdins, E. Liepins, M. Veilande, & M. Zviedris, "Ontology Enabled Graphical Database Query Tool for End-Users," in H.-M. Haav & A. Kalja, edd., Databases and Information Systems V (2009) 105-116.

* cited by examiner

METHOD AND PROCESS FOR SEMANTIC OR FACETED SEARCH OVER UNSTRUCTURED AND ANNOTATED DATA

CROSS-REFERENCE TO RELATED APPLICATIONS

The present application claims priority to U.S. Provisional Application No. 61/386,051, filed Sep. 24, 2010. The entire disclosure of that previous application is incorporated herein by reference.

FIELD OF THE INVENTION

The present invention relates to semantic searches over an annotated corpus of data.

BACKGROUND OF THE INVENTION

Modern pipelined text processing architectures are characterized by their open-ended, i.e., extensible, nature and by the high expressiveness of feature structure-based annotation schemes. Typically, text analytic pipelines seek to detect semantic elements in the underlying text repository, i.e., corpus, of documents. These semantic elements that represent portions of the documents are discovered using language analysis of the documents and are exposed or highlighted using semantic annotations associated with the semantic elements in the corpus of documents. While text analytics applications in a variety of information management scenarios facilitate arbitrarily deep and broad text analysis, these analyses often produce extremely dense annotation repositories where multiple levels of analysis get encoded to a given semantic elements as layered annotations.

The resulting layered annotations present challenges related to two use-case scenarios, i.e., cases where the annotations are being used to locate or to identify the desired semantic elements within a corpus of documents. The first use-case is where an analytics developer seeks to improve the actual detection of semantic annotations requiring deep language analysis. The second related use-case is where an end-user is trying to navigate a semantically annotated corpus and is seeking meaningful relationships between concepts in the domain that would be impossible to formulate in terms of a traditional keyword search. Faceted searches add to the complexity experienced by the end-user in searching the corpus of documents. A faceted search is distinct from a semantic search and involves progressively narrowing the range of choices in multiple dimensions. Therefore, the end-user is faced with the challenge of composing a complex query in multiple dimensions.

Systems for semantic search exist and include, for example, JURU (http://www.haifa.ibm.com/projects/imtl-juru/index.html). Search facilities, including, for example, Lucene (http://lucene.apache.org/java/docs/) and Indri (http://www.lemurproject.org/indril), provide keyword search, and not semantic search. These existing semantic search tools, however, employ text only searching and in some cases allow only a restricted specification of types. For example, items from a defined and finite set of types, "Author", "Title" or "Material", are selected from a drop-down menu. These existing systems do not allow for the graphical composition of queries or the use of semantic or conceptual queries, i.e., queries with no literal term.

SUMMARY OF THE INVENTION

Exemplary embodiments of the present invention are directed to methods and systems for specifying search terms for a semantic text search, which is a search through documents containing text or data labeled or marked with annotations. For example, on the text "Mary had a little lamb", the word "Mary" may have been marked with the label or meta data "person", and the word "lamb" may have been marked with the label "animal". In one embodiment, the search looks for nested labels, i.e., a search for a word that is marked with both a first label and a second label. In one embodiment, the search is specified using a graphical user interface.

In accordance with exemplary embodiments of the present invention, semantic queries of a corpus of data are conducted through the use of semantic annotations, for example, with rich internal feature-based structure, coupled with a graphical user interface. Therefore, the content behind concepts annotating something like the Semantic Web can be accessed.

DETAILED DESCRIPTION

Figure 1:
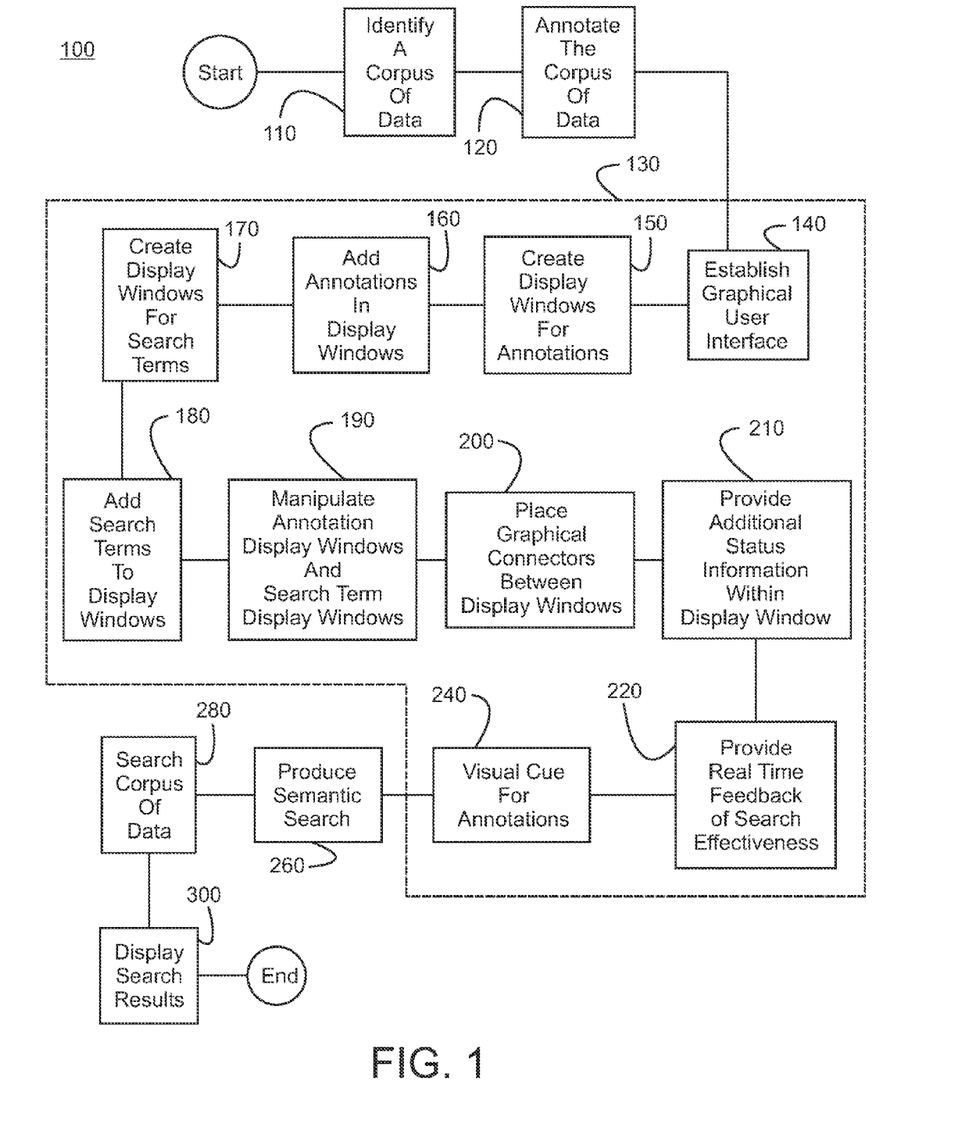
FIG. 1 is a flow chart illustrating an embodiment of a method for creating a semantic query in a graphical user interface in accordance with the present invention.

Systems and methods in accordance with exemplary embodiments of the present invention provide for improved searching of a corpus of data. This improved searching utilizes semantic queries that are assembled in a graphical user interface using search terms or keywords within the corpus of data in combination with annotations that are assigned to various portions of the corpus of data. Referring initially to FIG. 1, an embodiment of a method for creating and conducting semantic searches over a corpus of data 100 in accordance with the present invention is illustrated. Initially, a corpus of data to be searched is identified or assembled. In accordance with one embodiment, end users, e.g., domain experts, explore a given data compilation or a set of data compilations relevant to a given subject matter domain. These data compilations can be contained in one or more databases and are referred to as a corpus of data. As used herein, the corpus of data is representative or indicative of a given subject matter domain and the underlying semantics of that subject matter domain.

As stated, a given corpus of data is representative or indicative of a particular knowledge domain or subject matter domain. As used herein, a knowledge domain, subject matter domain or domain refers to a field of action, a field of endeavor, a field of thought or an area of knowledge. Therefore, all data compilations within a given corpus of data associated with a given domain are related to the field or area covered by that domain. In addition, the corpus of data is also indicative of or associated with the underlying semantics of the domain to which it is associated. Suitable domains include, but are not limited to, articles covering a given sport or sporting event, documentation related to a given class of machinery, e.g., user manuals, manuals associated with different classes of software applications and published articles covering the arts, sports or science. A given corpus of data contains a plurality of distinct data compilations that are all related to a common subject matter domain, e.g., sports, a particular event, a consumer product, a computer program, a historical figure, a culture, a historical event, a current event and a political event. Each data compilation includes information related to or relevant to the subject matter domain.

In order to facilitate semantic searches over the identified corpus of data, the identified or assembled corpus of data is annotated 120. Although annotations can be attached to the entire corpus of data or each individual data compilation within the corpus of data, preferably, annotations are assigned to individual data elements within the data compilations. Each data compilation includes a plurality of data elements, and each data element contains data. In one embodiment, a given data element contains at least a single datum. For example, the corpus of data is a collection of text documents or word processing documents. Each text document is a distinct data compilation within the corpus of data. A given portion, paragraph, sentence or word, of a word processing document represents a data element. Suitable data compilations, however, are not limited to text-based compilations and can include graphics, pictures, audio files, video files and computer code that relate to the common subject matter domain of the corpus of data. In a text-based data compilation, suitable data elements include, but are not limited to, any defined portion of a document, e.g., a word processing document or web page, such as chapters, paragraphs, sentences, words, headings, tables, charts and single characters, e.g., page numbers or other alpha-numeric characters, graphics, videos, hyperlinks, pictures or any portions of thereof. Any given word processing document can include a plurality of identified portions, i.e., a plurality of data elements, and the data elements can overlap. For example, a sentence can be a first data element and the paragraph containing that sentence can be a second data element.

The corpus of data is annotated by assigning at least one annotation to each data element within the data compilations that are to be annotated. Therefore, a given data element can have no associated annotations, one associated annotation or a plurality of associated annotations. In one embodiment, assembly of the corpus of data, identification of the data elements within the corpus of data and assignment of annotations to the data elements is accomplished by a domain expert using concept-labels specified by domain experts and stored in a database such as an index. The domain expert is knowledgeable of the subject matter domain for which the corpus of data is assembled. In one embodiment, the semantic queries constructed using the annotations are created by the domain expert in accordance with the systems and methods of the present invention. Alternatively, another person, e.g., an end user of the corpus of data, other than the domain expert creates the semantic queries. In one embodiment, the domain expert is the end user. The end users can be using the corpus of data to conduct research in the subject area domain or to look for information, e.g., user manuals, associated with a given product.

Suitable methods for annotating the data elements are known and available in the art. In general, annotations describe or categorize the content of the data elements. Therefore, as data elements are identified within the data compilations, the contents of the data elements are analyzed. Based on this analysis, suitable annotations or concept-labels are assigned to each data elements. These annotations provide a description or categorization of the contents of the data element. A given data element can have multiple associated annotations. The multiple annotations associated with a given data element can be arranged in a hierarchy, where two or more annotations can be contained by another annotation of the same data element. The data elements and associated annotations are then saved to a database or index for access and use during the creation of semantic queries over the corpus of data. Upon completion of the annotation, the previously unstructured corpus of data is annotated.

In one embodiment, the identified and assigned annotations are used to define an ontology for the corpus of data that contains the set of semantic types, i.e., the annotations, relationships among the semantic types, i.e., relationships among the annotations including containment by a first annotation of two or more additional annotations, and essential characteristics or properties of the semantic types. The ontology provides the basic vocabulary that is used to describe the semantic relations and is used in the construction of the semantic queries. The constructed semantic queries discover instances of associations between semantic types, i.e., annotations, as they are manifested in data elements that have in-context mentions of these semantic types. Therefore, a type system is defined. Then the domain expert or end user, desiring to search the index, composes a query, which extracts document fragments from the index and displays them appropriately in the context of the document and corpus. The end user conducting the search can be the same domain expert or another end user. Exemplary embodiments in accordance with the present invention cover the creation of the concept-oriented index, the composition of the query and the display of the extracted document fragments.

In order to analyze the data elements, annotate the data elements and construct the ontology, a basic set of analytics may is used. Suitable analytics include, but are not limited to, a tokenizer; a named entity detector and a shallow, or a deep, syntactic parser. These analytics identify and deposit instances of words (Tokens) and other types, i.e., semantics or annotations, that are of interest. Examples of these other types include, but are not limited to players, teams, software components, IT products, and authors, among others. Also identified are syntactic fragments including noun and verb phrases. All the identified types are deposited or saved in an annotation repository or database.

Having annotated the data elements in the corpus of data, stored the annotations and data elements in an index and used the annotations to construct an ontology, a semantic query using both the annotations and search terms contained within the data elements is constructed 130. Since the construction and expression of complex semantic search queries using annotations, search terms and relationships among the annotations and search terms is complex, graphical user interfaces are used to simplify the creation of the complex semantic search queries. Therefore, a graphical user interface is established on the display of a suitable computing system. Any suitable computing system capable of displaying graphical user interfaces can be used. In general, the graphical user interface is a screen on which graphical representations of annotations and search terms can be created, displayed and manipulated. The graphical user interface can be provided as part of a networked or web-based computer application or can be a local computer application that is resident on and executing on a local computing system.

The graphical user interface abstracts the complexity underlying the semantic search query language and simplifies the viewing of the semantic search results by retrieving data elements that satisfy the abstract query and by providing an improved presentation for the search results. Therefore, the graphical user interface provides for improvements in both constructing queries and displaying search results. The query extracts data elements, e.g., document fragments, from the index and displays these extracted data elements in the context of their associated data compilation and the corpus of data. Overall, the graphical user interface provides for a multi-dimensional visual spatial display of the semantic query. These multiple dimensions include a first dimension of term aggregation, a second dimension of search term containment and a third dimension of visual cues to differentiate annotations from search terms.

Initially, the graphical user interface is used to create an aggregation of graphical representations of annotations associated with a plurality of data elements contained within the corpus of data and graphical representations of search terms contained within the plurality of data elements. These graphical representations contain the desired annotations and search terms, e.g., keywords within the data elements, and can be moved or manipulated with respect to each other within the graphical user display environment. This aggregation represents the first dimension of the spatial display of the annotations and search terms to be included in the semantic query. Aggregation is a listing of all the desired annotations and search terms. Suitable graphical representations would facilitate entry and display of the desired annotation or search term into the graphical interface such that each annotation or search term is independently distinguishable and positionable within the graphical user interface with respect to the other graphical interfaces. In one embodiment, these graphical interfaces are separate and independent display windows for each annotation and search term.

In one embodiment, one or more display windows for annotations are created in the graphical user interface 150. These windows can be drawn using suitable input devices associated with computing systems. Alternatively, these windows are selected from a template of windows provided within the graphical user interface. Each display window is a separate and independent display window that is associated with one of the annotations and is configured to accept the entry of text or other alpha numeric data. An annotation is then inputted into each annotation display window 160. Each annotation is associated with one or more data elements within the corpus of data and describes or categorizes data contained in the data elements to which that annotation is associated. Suitable methods for entering the annotations include typing annotations into each created display window and selecting an annotation from an exposable drop-down list of annotations associated with each display window. This drop-down list of annotations can be populated, for example, from the index or ontology associated with the corpus of data. In one embodiment, each annotation is selected from the ontology associated with the common subject matter domain of the corpus of data. This ontology includes the set of semantic types descriptive of the common subject matter domain, relationships among the semantic types and properties of the semantic types. The ontology can be modified, for example by modifying the relationships among the semantics types, i.e., annotations, and the properties of the semantic types. This modification results in a modification to the expressed relationships among the annotations and the defined semantic query. Therefore, in addition to modifying the annotations and search terms within the semantic search in order to modify the semantic search, modifications to the semantic search can be achieved by modifying the ontology and not the semantic search, which effectively modifies the annotations in the same arrangement of annotations and search terms.

Similarly, search terms are added to the aggregation by creating one or more search term display windows in the graphical user interface 170. These display windows can be drawn using suitable input devices associated with computing systems. Alternatively, these windows are selected from a template of windows provided within the graphical user interface. Each display window is a separate and independent display window that is associated with one of the search terms and is configured to accept the entry of text or other alpha numeric data. One or more search terms are then inputted into each search term display window 180. Suitable methods for entering the search terms include typing search terms into each created display window and selecting a search term from an exposable drop-down list of search terms associated with each display window. In one embodiment, the annotation display windows, annotations, search term display windows and search terms are added one at a time, in series, as a more specific or refined semantic search is desired.

The resulting aggregation contains a plurality of the desired annotations associated with data elements in the corpus of data and a plurality of the desired search terms contained within the data elements in the corpus of data. Although the number of graphical representations of annotations can equal the number of graphical representation of search terms, it is not required to have a one-to-one correspondence between annotations and search terms. In one embodiment, the aggregation includes at least one annotation and at least one search term. The aggregation represents a simple listing or grouping of annotations and search terms.

The second dimension uses the entered graphical representations to provide a spatial illustration in the graphical user interface of the relationships among the graphical representations of the annotations and the graphical representations of the search terms. In one embodiment, the relative positions of the graphical representations of the annotations and the search terms within the aggregation are manipulated within the graphical user interface environment to express relationships among the annotations and search terms 190. This includes manipulating relative positions of the graphical representations within the graphical user interface relative to each other to generate a visual spatial representation of the semantic query.

In one embodiment, the visual spatial representation among the annotations and search terms is enhanced by placing graphical connectors between pairs of display windows 200. Each graphical connector represents a predefined relationship between a given pair of display windows. Suitable graphical connectors include lines or arrows between pairs of windows. The graphical connectors also include logical operators including Boolean logical operators such as "and", "or" and "nor", among others. These graphical connectors express logical relationships among annotations and search terms that are not expressed by the annotations in one of the annotation display windows. The graphical connectors provide a visual indication of the relationships between annotations and search terms as well as the relationships between different annotations. Therefore, in one embodiment, graphical connectors are placed between a display window containing an annotation and a display window containing a search term, and in another embodiment, graphical connectors are placed between pairs of display windows where each window in each pair of windows contains an annotation.

By moving the display windows relative to each other within the graphical user interface, the display windows are arranged into a hierarchy having child nodes and ancestor nodes. In one embodiment, display windows containing annotations represent ancestor nodes to display windows containing search terms, which represent child nodes in the hierarchy. A semantic search created using this hierarchy is searching for a data element or data elements that are annotated with the ancestor node annotation and that contain the data or keywords as expressed in the child node search term display window. Two or more separate display windows each containing an annotation can also be covered by or contained within an annotation associated with another display window. Therefore, at least one display window in the hierarchy containing an annotation represents a common ancestor node to two or more additional display windows each containing an annotation.

In general, the graphical representations of annotations are moved relative to each other to express relationships between two or more graphical representations of annotations. These relationships are contained or are expressed in one of the graphical representations of the annotations. In one embodiment, the graphical representation of a given annotation is moved relative to two or more additional graphical representations of annotations to assign an attribute of the given annotation to the additional annotations. In these embodiments, the attributes or relationships expressed in a first annotation display window are applied to other annotation display windows or search term display windows. This can be differentiated from the use of graphical connectors that apply logic between graphical representations that is external to the logic contained in the annotation graphical representation. The attributes and relationships contained within the graphical representations include verbs or actions that are applied between annotations and search terms that are nouns and facts that are expressed between or among annotations and search terms that are nouns.

In one embodiment, additional status information related to a given annotation or search term is provided within the graphical representation or display window associated with that annotation or search term 210. For example, additional alpha-numeric or graphical icons are provided within each graphical representation to mark the annotation or search term associated with that graphical representation as either a required or excluded term in the semantic search. These graphical icons include, for example. "+" and "−"signs. In order to improve the quality of the resultant semantic search and to assist the end user or domain expert in selecting the most efficacious annotations, search terms and relationships, real time visual feedback is provided to the end user or domain expert during use of the graphical user interface to create the graphical representations and to manipulate the relative positions of the graphical representations 220. This feed back provides visual prompts that indicate an effectiveness of the resulting semantic search over the corpus of data. These visual prompts include alpha-numeric prompts, color changes, font changes and the display of a calculated effectiveness metric. The system monitors the entered annotations and search terms as well as the established relationships among the annotations and search terms and analyzes the effectiveness of each subpart of the semantic search, i.e., each annotation, search term and relationship, as it is entered or created. This analysis is immediately reported to the semantic search creator and can be logged for future reference and use.

A third dimension of the visual spatial display of the semantic query representation within the graphical user interface is also provided. This third dimension provides a graphical distinction between graphical representations of annotations and graphical representations of search terms. In particular, a visual cue is provided in association with graphical representations associated with annotations 240 to differentiate these graphical representations associated with annotations from graphical representations associated with search terms. This reduces or eliminates confusion when manipulating graphical representations within the graphical user interface to create the desired hierarchy. A quick look at the resultant hierarchy indicates which graphical representations are annotations and which are search terms. Suitable visual cues include, but are not limited to, changes in colors, shapes, font sizes or text sizes within the graphical representation associated with annotations.

The annotations, search terms and expressed relationships define the semantic query. Therefore, once the graphical representations, annotations and search terms are entered and manipulated, a resulting semantic search is produced 260. This resulting semantic search is used to search the corpus of data 280. The results of this search are then displayed to the end user, preferably using the same graphical user interface that created the semantic search. Based on the results of the search, the visual spatial semantic search representation can be saved or can be adjusted to modify the resulting semantic search. In addition, the ontology associated with the subject matter domain of the corpus of data being searched can be modified to modify the results or effectiveness of the resulting semantic search.

Given one or more corpora that have been annotated in accordance with the present invention, end users compose queries using types, i.e., annotations, known to be found in the corpus of data either by drag-and-drop from a display of the types, by word-completion when entering the name of the type or by any other suitable means. The process of expressing complex semantic search queries in terms of annotations, search terms, i.e., keywords within the data elements, and relations is simplified through the use of a graphical interface that abstracts the complexity of underlying semantic search query languages and simplifies the viewing of semantic search results by retrieving data such as documents and passages that satisfy the abstract query. In general, annotations that are of interest to a searcher or search creator, e.g., the domain expert or end user, and that are used to explore the annotated corpus of data cover a wide variety. In one embodiment, a searcher of the annotated corpus of data is looking for data elements within this corpus where annotations are used in combination. These data elements have two or more associated annotations. This combination of annotations may simply be a collection, aggregation or grouping of annotations. Alternatively, the annotations of a given data element are combined into more complex relationships. Queries are constructed to leverage the complexity of the annotations in locating the desired data elements.

Exemplary embodiments of systems and methods in accordance with the present invention utilize the graphical user interface to compose semantic queries containing annotations associated with data elements in a corpus of data. Semantic queries over the corpus of data can be composed iteratively and incrementally, and the graphical user interface displays the current status of the query. Optionally, a background process can update a display indicating the presence and number of passages or documents found for the query in its current state, for example in real time during creation of the semantic query.

In one embodiment, the visual spatial display of the query is referred to as the "query-map". When the query is complete, the end user requests a search, which yields a list of the results displayed as either data elements containing the desired search terms and having the associated annotations or data compilations containing one or more such data elements. A variety of methods can be used to extract the data elements from the data compilations of the corpus of data. In one embodiment, the data elements are meaningful sub-sections of text or data containing the desired search terms and having the associated desired annotations. The search results can be referred to as "hits" within the corpus of data, and the display of the hits includes some portion of the data found. For example, all of the data can be displayed if what was found was a brief passage. Additional information can also be provided with the displayed hits including, but not limited to, the data compilation in which a given hit was found, a rating of the quality of the hit, where higher ratings refer to hits that by some metric more closely match the query, and some information about the annotations found in that hit. The display of the hits can also be provided with sorting and filtering options to facilitate inspection of the hits.

Referring to FIGS. 2-11, an exemplary embodiment of using the graphical user interface to construct a complex semantic query over a corpus of data is illustrated. In this embodiment, a corpus of data is defined covering the subject matter of novels and movies based on those novels. The corpus of data includes, among other data compilations, the novels, audio and video files related to the movies, reports and reviews on the movies, articles and other test documents related to the novels or movies and any other compilations of data related to the movies and novels. The various data compilations are analyzed, and data elements are identified Annotations or semantic types relevant to the subject matter of the corpus of data are determined and are associated with the identified data elements. This information is stored in an index and an appropriate ontology is created. The annotated corpus of data can now be search using both the annotations in the ontology and search terms in the data elements.

Figure 2:
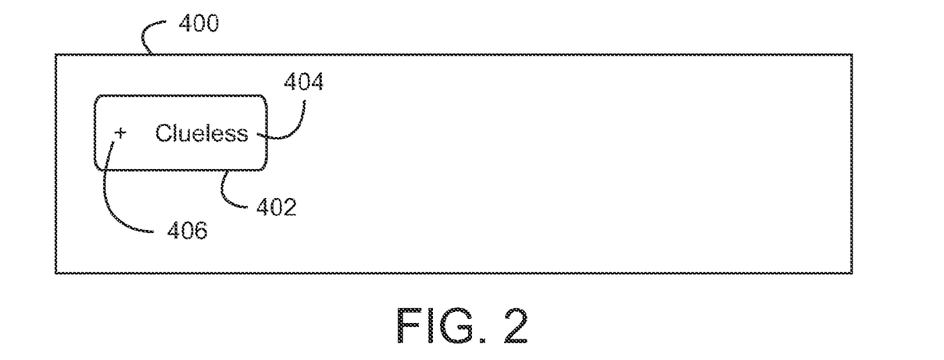
FIG. 2 is a representation of an embodiment of a graphical user interface environment containing a representation of a visual spatial display of a semantic search in accordance with the present invention.

As shown in FIG. 2, an instance of the graphical user interface environment 400 is provided on the display of a suitable computing system. This environment provides the space or template on which the visual spatial display of the semantic query is constructed. An aggregation of annotations and search terms is created by first entering the desired graphical representations of the annotations and search terms. The end user is looking for data related to the book *Emma* and any movie that was created based on that book. The end user first enters a search term that is a literal word or keyword of the search and is the name of the movie, i.e., "Clueless", based on the book. In order to do this, the end user selects from a displayed menu or alternatively draws a search term display window 402 in the graphical user interface environment 400. Suitable methods for drawing or selecting the appropriate type and style of display window are known and available in the art. As illustrated, the search term display window 402 is a generally rectangular window. Into this search term display window 402, the end user inserts the search term "Clueless" 404. In addition, a graphical icon 406 is included in the search term display window 402 adjacent the search term. The graphical icon is a "+" symbol, indicating that the search term is required. This simple search will produce all data elements containing the word clueless whether associated with a movie title or just describing the foolish behavior of an individual. Therefore, further refinement is required to only search those data elements that use the term clueless as the title to a motion picture. According to the ontology, such data elements are labeled with the annotation "Movie Title".

Figure 3:
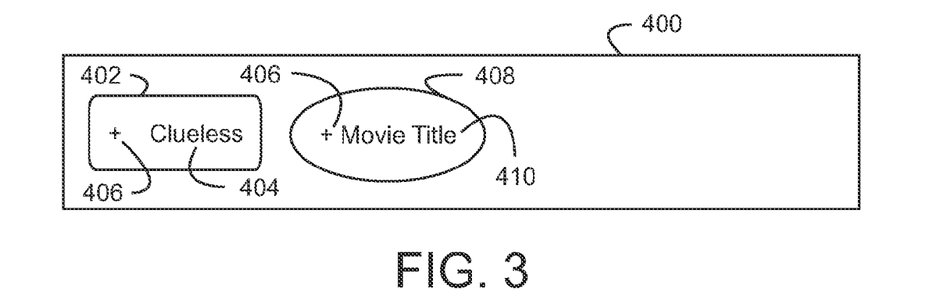
FIG. 3 is a representation of an embodiment of a graphical user interface environment containing another representation of a visual spatial display of a semantic search in accordance with the present invention.

Therefore, as shown in FIG. 3, the end user selects from a displayed menu or draws an annotation display window 408 in the graphical user interface environment 400. Suitable methods for drawing or selecting the appropriate type and style of display window are known and available in the art. As illustrated, the annotation display window 408 is a generally circular or oval window as distinguished from the generally rectangular display window of the search terms. This represents what was previously discussed as the third visual and spatial dimension of the semantic query display, the visual cue for graphical representations of annotations. In this case, the annotation display is differentiated by the visual cue of shape. Other visual cues can be provided by shading within the display window or by the use of a different color. Into this annotation display window 408, the end user inserts the annotation "Movie Title"410. In addition, the graphical icon 406 is also included in the annotation display window 408 adjacent the annotation. Again, the graphical icon is a "+" symbol, indicating that the annotation is required. Now the semantic query will search for any data element containing the search term clueless and any data element annotated as a movie title. However, this is a simple aggregation of search elements that will again yield all data elements containing the word clueless and all movie title data elements regardless of the actual title of the movie. Therefore, a relationship is required between the annotation and the search term.

Figure 4:
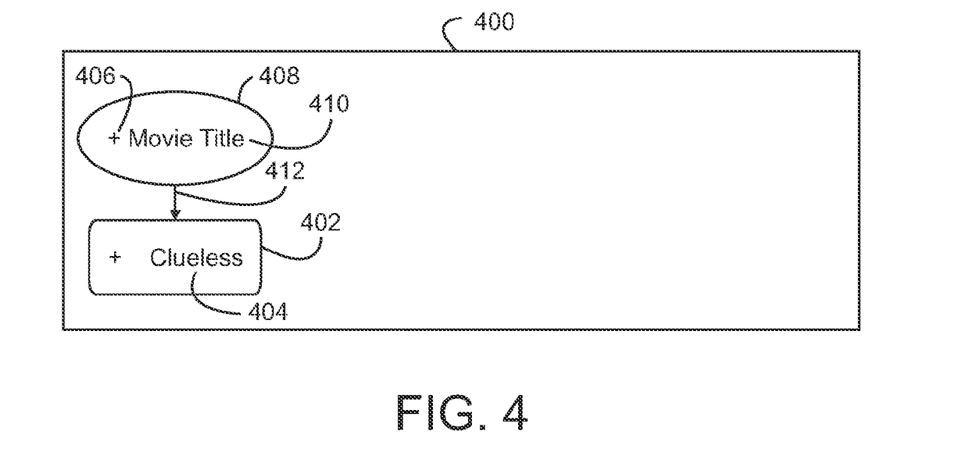
FIG. 4 is a representation of an embodiment of a graphical user interface environment containing another representation of a visual spatial display of a semantic search in accordance with the present invention.

This relationship utilizes the second dimension of the visual spatial display of the present invention where containment of one graphical representation by another graphical representation is illustrated. This is accomplished using the ability within the graphical user interface environment 400 to move the graphical representations, and therefore the annotations and search terms associated with these graphical representations with respect to each other. This forms a hierarchy, and as shown in FIG. 4, the annotation display window 408 is a parent node in the hierarchy to the search term display window 402. Therefore, the semantic search will look for data elements labeled movie title that also contain the search term clueless. A graphical connector 412 is also provided between the two display windows in the hierarchy, illustrating that the search term is contained within the annotation. This type of graphical connector applies the attributes of the annotation to the search term. Although illustrated with the steps shown in FIGS. 2-4, embodiments of the present invention can go directly from FIG. 2 to FIG. 4, without creating the aggregation illustrated in FIG. 3. In general, the present invention provides for building the semantic query using aggregation, containment and visual cues in any desired order.

Figure 5:
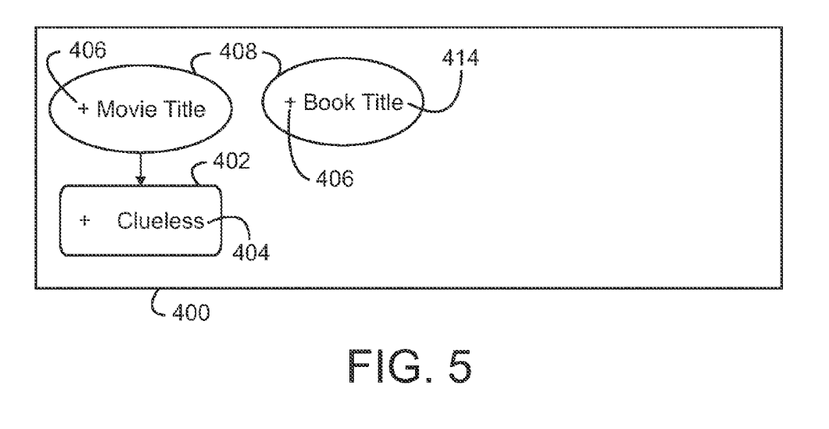
FIG. 5 is a representation of an embodiment of a graphical user interface environment containing another representation of a visual spatial display of a semantic search in accordance with the present invention.
Figure 6:
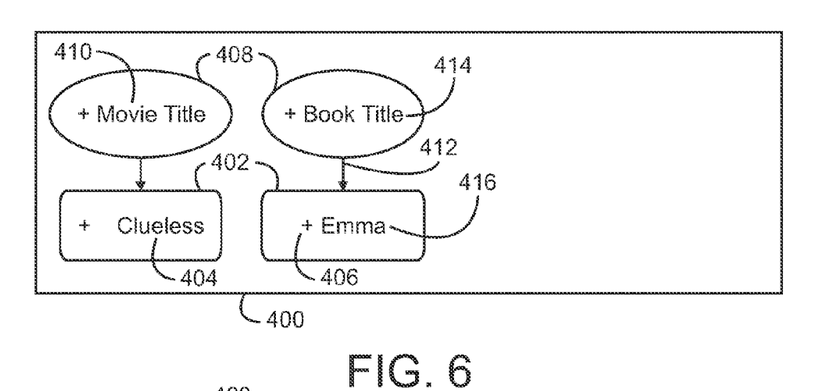
FIG. 6 is a representation of an embodiment of a graphical user interface environment containing another representation of a visual spatial display of a semantic search in accordance with the present invention.
Figure 7:
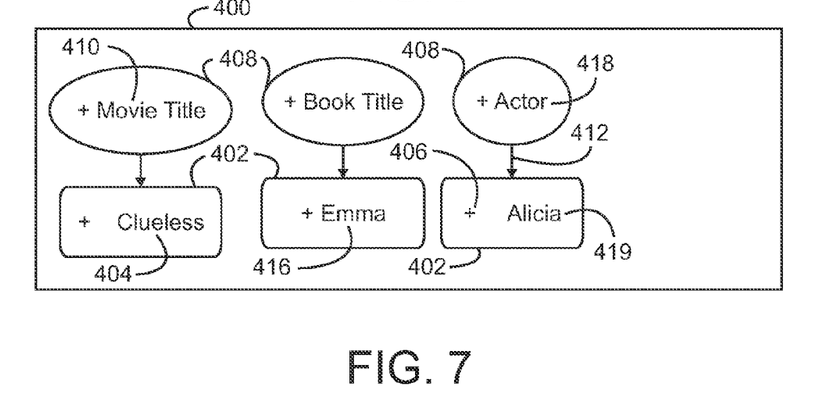
FIG. 7 is a representation of an embodiment of a graphical user interface environment containing another representation of a visual spatial display of a semantic search in accordance with the present invention.

In order to find data elements that discuss both the movie Clueless and the book titled *Emma* on which the movie is based, additional search terms are required. As shown in FIG. 5, another annotation display window 408 is added to the graphical user interface. Into this annotation display window 408, the book title annotation 414 is added. In this step, the annotation is added first before a search term is added. This will uncover movie title data elements containing clueless and all book title data elements. Therefore, as shown in FIG. 6, a search term display window 402 is added, and the search term Emma 416 is added to the display window. The two display windows are moved into the desired spatial arrangement, and a graphical connector 412 is placed between the two display windows. This search will now also return data elements annotated as book titles containing the word Emma. The graphical interface of the present invention provides the flexibility to add the display windows in any desired order and to reposition those display windows to create the desired hierarchy and semantic query.

Figure 8:
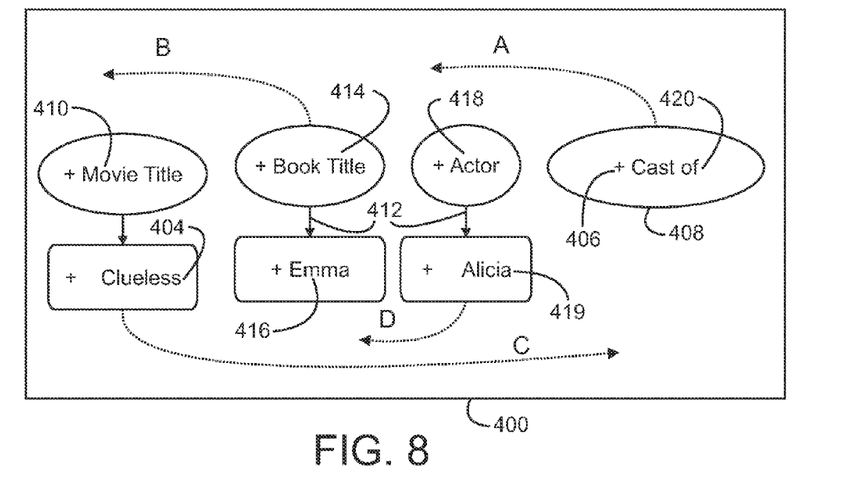
FIG. 8 is a representation of an embodiment of a graphical user interface environment containing another representation of a visual spatial display of a semantic search in accordance with the present invention.

If multiple movies titled "Clueless" exist in the corpus of data, then refinement of the semantic search is needed. For example, the names of the cast members can be included to differentiate the various movies. At show in FIG. 7, another hierarchy of an annotation display window 408 and a search term display window 402 is added and connected by a graphical connector 412. The annotation actor 418 is added to the annotation display window, and the search term Alicia 419 is added to the search term display window. This will provide additional search results that include any actor data element containing the name Alicia. It is desired to tie that actor into the cast of the movie Clueless. Therefore, as shown in FIG. 8, an annotation window 408 is added with the "cast of" annotation 420. The graphical user interface is then used to assemble the desired hierarchy among the elements. The "cast of " annotation window is moved within the graphical user interface environment in the direction of arrow A. The "Actor" annotation and Alicia search term window hierarchy is moved within the graphical user interface environment in the direction of arrow D. The "Book Title" annotation and Emma search term window hierarchy is moved within the graphical user interface environment in the direction of arrow B. The "Movie Title" annotation and Clueless search term window hierarchy is moved within the graphical user interface environment in the direction of arrow C.

Figure 9:
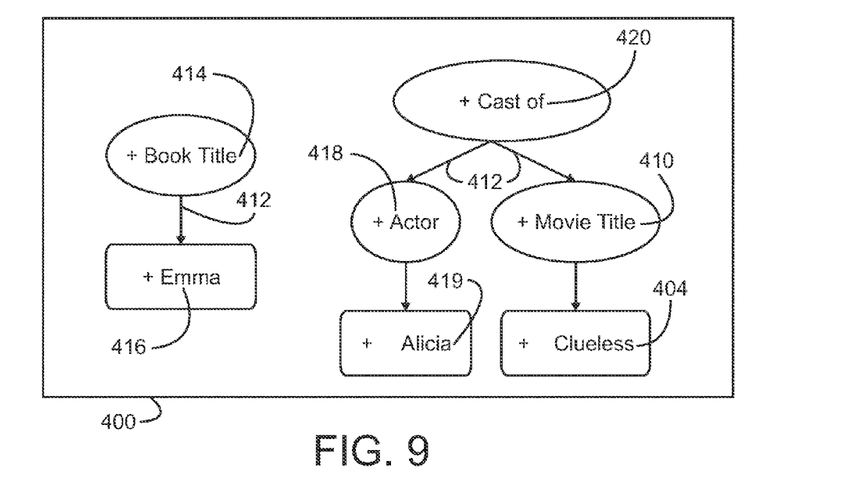
FIG. 9 is a representation of an embodiment of a graphical user interface environment containing another representation of a visual spatial display of a semantic search in accordance with the present invention.
Figure 10:
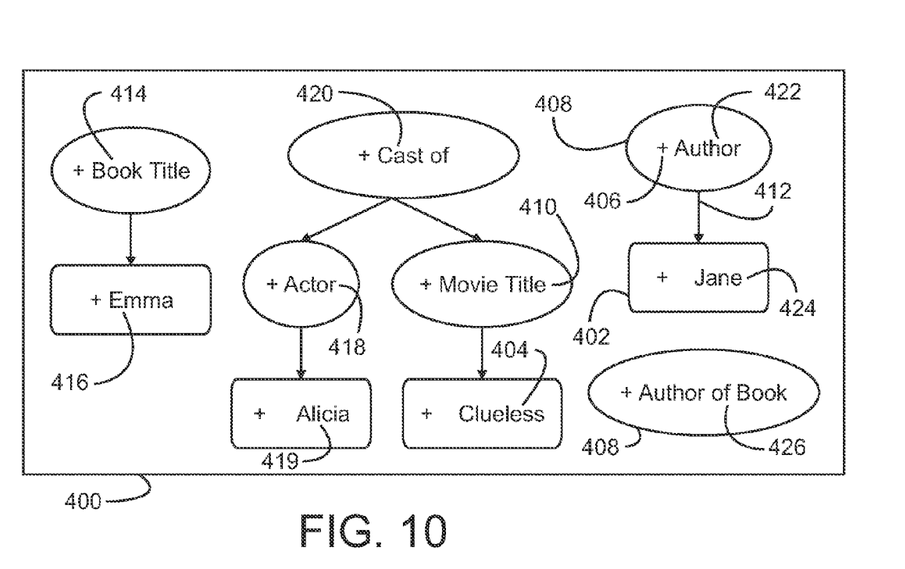
FIG. 10 is a representation of an embodiment of a graphical user interface environment containing another representation of a visual spatial display of a semantic search in accordance with the present invention.
Figure 11:
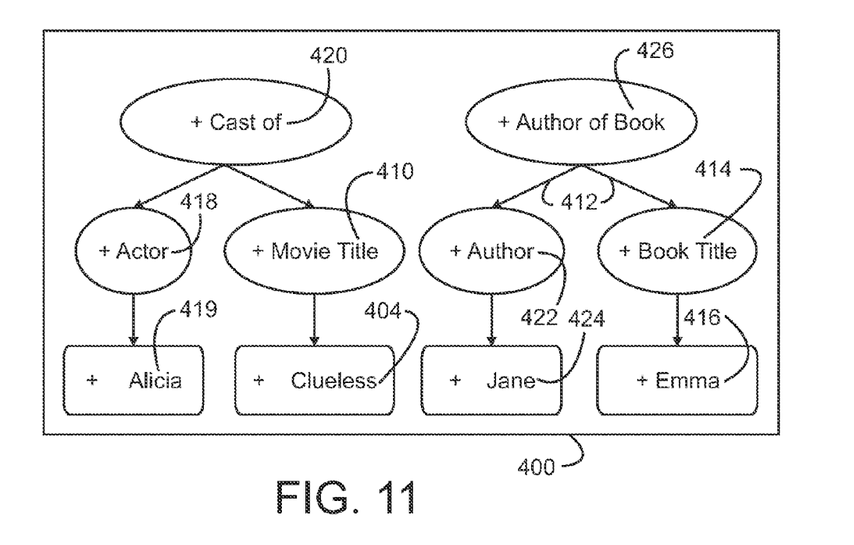
FIG. 11 is a representation of an embodiment of a graphical user interface environment containing another representation of a visual spatial display of a semantic search in accordance with the present invention.

The result of these manipulations is illustrated in FIG. 9. A hierarchy is produced where both the "Actor" annotation 418 and the "Movie Title" annotation 410 as well as the associated search terms are contained within the "Cast of" annotation 420, as indicated by their spatial positioning and the graphical connectors 412. This semantic search will return data elements annotated as "Book Title" with the term Emma, as well as data elements labeled with the annotations "Cast of" and "Actor" with the term Alicia and "Cast of" and "Movie Title" with the term Clueless. This is more specific semantic search. A similar specificity can be added to the semantic search with regard to the book. As shown in FIG. 10, the annotation display window 408 with the annotation "Author" 433 is added with the connected child node being a search term display window 402 containing the search term Jane 424. To connect all of these book related search terms, another annotation display window is added with the annotation "Author of Book" 426. These elements are manipulated within the graphical user interface environment 400 to yield the visual spatial display of the semantic search shown in FIG. 11. In addition to the data element described above, this semantic search will also return data elements containing both Jane and Emma where Jane is the name of the author of the book titled Emma. This completed arrangement of search elements can then be converted into the semantic search that is used to search the corpus of data.

Figure 12:
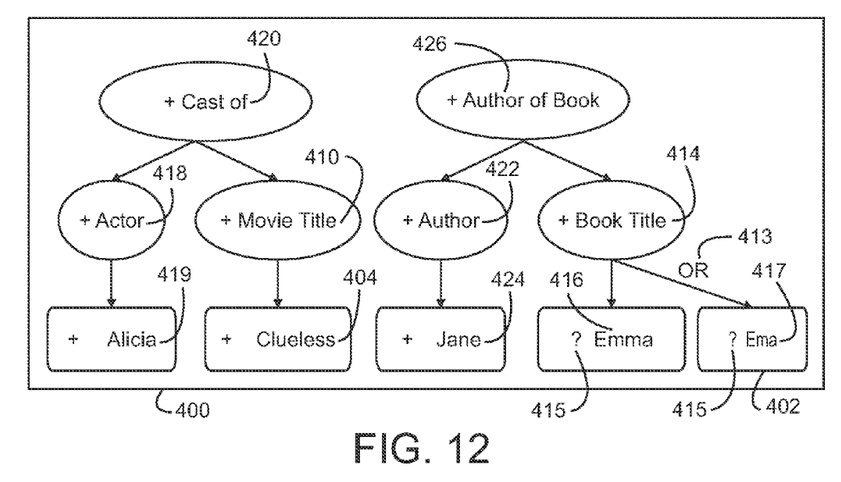
FIG. 12 is a representation of an embodiment of a graphical user interface environment containing another representation of a visual spatial display of a semantic search in accordance with the present invention.

Referring to FIG. 12, after conducting the semantic search and reviewing the search results, the semantic search can be modified to improve the results. For example, a determination is made that the number of data elements containing a book titled Emma by an author named Jane is unexpectedly low. It is then determined that there may be an alternative spelling or a misspelling of the title of the book. Therefore, an additional search term display window 402 is added with the search term Ema 417. This is included as a second child node of the Book Title annotation 414 node. In addition, a graphical connection 413 is added between the new search term display node 417 and the parent annotation display node 414. This graphical connection 413 includes logic external to the contents of the annotation display window, in this case the logical "or". Therefore, the book title can be Emma or Ema. In addition, the additional status information is changed to a "?" symbol 415 from the "+" symbol in one or more of the search term display windows. This indicates that the search terms are not required but optional. The visual spatial representation can be further modified as desired to improve the quality of the semantic search results obtained.

In another embodiment, the present invention is directed to a method of searching a collection of annotated documents, i.e., a corpus of data, using a visual or graphical user interface by creating a first search term display window within the graphical user interface environment that contains at least one search term. In addition, a first annotation display window is created within the graphical user interface window that contains an annotation label. In one embodiment, the first annotation display window is created by an end user selecting the desired annotation from a list of annotation labels that is shown on the screen of the graphical user interface. The first search term display window is connected to the first annotation display window to create a relationship between the two windows. The collection of annotated documents is searched to identify an element in one of the documents that is marked with the annotation label from the first annotation display window and that includes the search term in the first search term display window. Each document contains elements at least one of which is marked with an annotation, and each element includes at least one word. Each annotation is a label that is applied to marked elements.

A second annotation display window can also be created in the graphical user interface. This second annotation display window contains an annotation label. The second annotation display window is connected to the first annotation display window to create a relationship between the first annotation display window and second annotation display window. The collection of documents or files is searched to identify an element in one of the documents that is marked with the annotation label in the first annotation display window, marked with the annotation label in the second annotation display window and that includes the search term in the first search term display window. In one embodiment, a second search term display window is created on the screen of the graphical user interface and this display window contains a least one search term. In addition, a second annotation display window is created on the screen of the graphical user interface and this display window contains an annotation label. The second search term display window is connected to the second annotation display window to create a relationship between the first search term display window and first annotation display window. The collection of annotated documents is searched to identify an element in one of the documents that contains a first element that is marked with the annotation label in the first annotation display window and the search term in the first search term display window as well as a second element that is marked with the annotation label in the second annotation display window and that includes the search term in the second search term display window.

In one embodiment, the connection between the first search term display window and the first annotation display window is moved to instead connect the first search term display window to the second annotation display window to create a relationship between the first search term display window and second annotation display window. In addition, the connection between the second search term display window and the second annotation display window is moved to instead connect the second search term display window to the first annotation display window to create a relationship between the second search term display window and first annotation display window. The collection of annotated documents is searched to identify an element in one of the documents that contains a first element that is marked with the annotation label in the first annotation display window and that includes the search term in the second search term display window. In addition, the results contain a second element that is marked with the annotation label in the second annotation display window and that includes the search term in the first search term display window.

As will be appreciated by one skilled in the art, aspects of the present invention may be embodied as a system, method or computer program product. Accordingly, aspects of the present invention may take the form of an entirely hardware embodiment, an entirely software embodiment (including firmware, resident software, micro-code, etc.) or an embodiment combining software and hardware aspects that may all generally be referred to herein as a "circuit," "module" or "system." Furthermore, aspects of the present invention may take the form of a computer program product embodied in one or more computer readable medium(s) having computer readable program code embodied thereon.

Any combination of one or more computer readable medium(s) may be utilized. The computer readable medium may be a computer readable signal medium or a computer readable storage medium. A computer readable storage medium may be, for example, but not limited to, an electronic, magnetic, optical, electromagnetic, infrared, or semiconductor system, apparatus, or device, or any suitable combination of the foregoing. More specific examples (a non-exhaustive list) of the computer readable storage medium would include the following: an electrical connection having one or more wires, a portable computer diskette, a hard disk, a random access memory (RAM), a read-only memory (ROM), an erasable programmable read-only memory (EPROM or Flash memory), an optical fiber, a portable compact disc read-only memory (CD-ROM), an optical storage device, a magnetic storage device, or any suitable combination of the foregoing. In the context of this document, a computer readable storage medium may be any tangible medium that can contain, or store a program for use by or in connection with an instruction execution system, apparatus, or device.

A computer readable signal medium may include a propagated data signal with computer readable program code embodied therein, for example, in baseband or as part of a carrier wave. Such a propagated signal may take any of a variety of forms, including, but not limited to, electro-magnetic, optical, or any suitable combination thereof. A computer readable signal medium may be any computer readable medium that is not a computer readable storage medium and that can communicate, propagate, or transport a program for use by or in connection with an instruction execution system, apparatus, or device.

Program code embodied on a computer readable medium may be transmitted using any appropriate medium, including but not limited to wireless, wireline, optical fiber cable, RF, etc., or any suitable combination of the foregoing.

Computer program code for carrying out operations for aspects of the present invention may be written in any combination of one or more programming languages, including an object oriented programming language such as Java, Smalltalk, C++ or the like and conventional procedural programming languages, such as the "C" programming language or similar programming languages. The program code may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider).

Aspects of the present invention are described above with reference to flowchart illustrations and/or block diagrams of methods, apparatus (systems) and computer program products according to embodiments of the invention. It will be understood that each block of the flowchart illustrations and/or block diagrams, and combinations of blocks in the flowchart illustrations and/or block diagrams, can be implemented by computer program instructions. These computer program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks.

These computer program instructions may also be stored in a computer readable medium that can direct a computer, other programmable data processing apparatus, or other devices to function in a particular manner, such that the instructions stored in the computer readable medium produce an article of manufacture including instructions which implement the function/act specified in the flowchart and/or block diagram block or blocks.

The computer program instructions may also be loaded onto a computer, other programmable data processing apparatus, or other devices to cause a series of operational steps to be performed on the computer, other programmable apparatus or other devices to produce a computer implemented process such that the instructions which execute on the computer or other programmable apparatus provide processes for implementing the functions/acts specified in the flowchart and/or block diagram block or blocks.

The flowchart and block diagrams in the Figures illustrate the architecture, functionality, and operation of possible implementations of systems, methods and computer program products according to various embodiments of the present invention. In this regard, each block in the flowchart or block diagrams may represent a module, segment, or portion of code, which comprises one or more executable instructions for implementing the specified logical function(s). It should also be noted that, in some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts, or combinations of special purpose hardware and computer instructions.

In one embodiment, the present invention is directed to a machine-readable or computer-readable storage medium containing a machine-executable or computer-executable code that when read by a machine or computer causes the machine or computer to perform a method for constructing a semantic query over a corpus of data in accordance with exemplary embodiments of the present invention and to the computer-executable code itself The machine-readable or computer-readable code can be any type of code or language capable of being read and executed by the machine or computer and can be expressed in any suitable language or syntax known and available in the art including machine languages, assembler languages, higher level languages, object oriented languages and scripting languages. The computer-executable code can be stored on any suitable storage medium or database, including databases disposed within, in communication with and accessible by computer networks utilized by systems in accordance with the present invention and can be executed on any suitable hardware platform as are known and available in the art including the control systems used to control the presentations of the present invention.

While it is apparent that the illustrative embodiments of the invention disclosed herein fulfill the objectives of the present invention, it is appreciated that numerous modifications and other embodiments may be devised by those skilled in the art. Additionally, feature(s) and/or element(s) from any embodiment may be used singly or in combination with other embodiment(s) and steps or elements from methods in accordance with the present invention can be executed or performed in any suitable order. Therefore, it will be understood that the appended claims are intended to cover all such modifications and embodiments, which would come within the spirit and scope of the present invention.

What is claimed is:

1. A method for constructing a semantic query over a corpus of data, the method comprising:
   using a graphical user interface to create an aggregation of graphical representations of annotations associated with a plurality of data elements contained within the corpus of data and graphical representations of search terms contained within the plurality of data elements, by:
      creating a separate display window within the graphical user interface for each annotation and for each search term; and
      entering an annotation or search term into each display, wherein the aggregation comprises at least one annotation and at least one search term;
   manipulating relative positions of the graphical representations of the annotations and the search terms within the aggregation within the graphical user interface to express relationships among the annotations and search terms by moving the display windows within the graphical user interface relative to each other to generate a visual spatial representation of the semantic query, the annotations, search terms and expressed relationships defining the semantic query; and
   searching the corpus of data using the defined semantic query.

2. The method of claim 1, wherein all data in the data elements of the corpus of data are representative of a common subject matter domain and the underlying semantics of that common subject matter domain.

3. The method of claim 2, wherein the step of using the graphical user interface further comprises selecting each annotation from an ontology associated with the common subject matter domain, the ontology comprising a set of semantic types descriptive of the common subject matter domain, relationships among the semantic types and properties of the semantic types.

4. The method of claim 3, wherein the method further comprises modifying at least one of the relationships among the semantic types and the properties of the semantic types in the ontology to modify the expressed relationships among the annotations and the defined semantic query.

5. The method of claim 1, wherein each annotation is associated with one or more data elements within the corpus of data and describes or categorizes data contained in the data elements to which that annotation is associated.

6. The method of claim 1, wherein the step of entering an annotation or search term into each display window further comprises at least one of typing an annotation or search term into a given display window and selecting an annotation or search term from an exposable drop-down list of annotations and search terms associated with each display window.

7. The method of claim 1, further comprising placing graphical connectors between pairs of display windows, each graphical connector representing a predefined relationship between a given pair of display windows.

8. The method of claim 7, wherein the step of placing the graphical connectors between pairs of display windows comprises placing graphical connectors between a display window containing an annotation and a display window containing a search term and placing a graphical connector between a pair of display windows each of which contains an annotation.

9. The method of claim 1, wherein the step of moving the display windows further comprises arranging the display windows into a hierarchy, wherein display windows containing annotations represent ancestor nodes to display windows comprising search terms.

10. The method of claim 9, wherein at least one display window in the hierarchy represents a common ancestor node to two additional display windows each containing an annotation.

11. The method of claim 1, wherein the method further comprises using at least one of alpha-numeric and graphical icons within each graphical representation to mark the annotation or search term associated with that graphical representation as either a required or excluded term in the semantic search.

12. The method of claim 1, wherein the method further comprises providing real time visual feedback during use of the graphical user interface to create the graphical representations and to manipulate of the relative positions of the graphical representations that indicates an effectiveness of the resulting semantic search over the corpus of data.

13. The method of claim 1, wherein the method further comprises using a visual cue in association with graphical representations associated with annotations to differentiate the graphical representations associated with annotations from graphical representations associated with search terms.

14. The method of claim 13, wherein the visual cue comprises changes in color, shape, font size or text size within the graphical representation associated with annotations.

15. The method of claim 1, wherein the step of manipulating relative positions of the graphical representations further comprises moving the graphical representation of a given annotation relative to two or more additional graphical representations of annotations to assign an attribute of the given annotation to the additional annotations.

16. A method for constructing a semantic query over a corpus of data, the method comprising:

using a graphical user interface to create an aggregation of graphical representations of annotations associated with a plurality of data elements contained within the corpus of data and graphical representations of search terms contained within the plurality of data elements, wherein the aggregation comprises at least one annotation and at least one search term;

manipulating relative positions of the graphical representations of the annotations and the search terms within the aggregation within the graphical user interface to express relationships among the annotations and search terms by moving graphical representations of annotations to express a relationship between two or more graphical representations of annotations, the annotations, search terms and expressed relationships defining the semantic query; and searching the corpus of data using the defined semantic query.

17. The method of claim 16, wherein the relationship is contained in one of the graphical representations of the annotations.

18. A non-transitory computer-readable storage medium containing a computer-readable code that when read by a computer causes the computer to perform a method for configuring a memory subsystem of a computing system, the method comprising:

using a graphical user interface to create an aggregation of graphical representations of annotations associated with a plurality of data elements contained within the corpus of data and graphical representations of search terms contained within the plurality of data elements, wherein the aggregation comprises at least one annotation and at least one search term;

manipulating relative positions of the graphical representations of the annotations and the search terms within the aggregation within the graphical user interface to express relationships among the annotations and search terms by moving graphical representations of annotations to express a relationship between two or more graphical representations of annotations, the annotations, search terms and expressed relationships defining the semantic query; and searching the corpus of data using the defined semantic query.

19. The non-transitory computer readable storage medium of claim 18, wherein the step of using the graphical user interface to create an aggregation further comprises creating the graphical representations of the annotations and search terms by:

creating a separate display window within the graphical user interface for each annotation and for each search term; and entering an annotation or search term into each display window.

20. The non-transitory computer readable storage medium of claim 19, wherein:

the step of manipulating relative positions of the graphical representations further comprises moving the display windows within the graphical user interface relative to each other to generate a visual spatial representation of the semantic query; and the method further comprises placing graphical connectors between pairs of display windows, each graphical connector representing a predefined relationship between a given pair of display windows.

21. The non-transitory computer readable storage medium of claim 18, wherein the method further comprises using a visual cue in association with graphical representations associated with annotations to differentiate the graphical representations associated with annotations from graphical representations associated with search terms.

22. The non-transitory computer readable storage medium of claim 18, wherein the step of manipulating relative positions of the graphical representations further comprises moving the graphical representation of a given annotation relative to two or more additional graphical representations of annotations to assign an attribute of the given annotation to the additional annotations.

* * * * *